US007012171B2

(12) United States Patent
Burrell

(10) Patent No.: US 7,012,171 B2
(45) Date of Patent: Mar. 14, 2006

(54) MODIFICATION OF PLANT METABOLISM

(75) Inventor: Michael Meyrick Burrell, Derbyshire (GB)

(73) Assignee: Advanced Technologies Cambridge Limited, Cambridge (GB)

( * ) Notice: Subject to any disclaimer, the term of this patent is extended or adjusted under 35 U.S.C. 154(b) by 0 days.

(21) Appl. No.: 11/196,155

(22) Filed: Aug. 2, 2005

(65) Prior Publication Data

US 2005/0268356 A1    Dec. 1, 2005

Related U.S. Application Data

(63) Continuation of application No. 08/284,199, filed on Aug. 2, 1994, now abandoned, which is a continuation of application No. 07/991,451, filed on Dec. 16, 1992, now Pat. No. 5,387,756, which is a continuation of application No. 07/628,216, filed on Dec. 17, 1990, now abandoned.

(30) Foreign Application Priority Data

Dec. 21, 1989 (GB) .................................. 8928937
Jul. 6, 1990 (GB) .................................. 9014988

(51) Int. Cl.
C12N 15/54    (2006.01)
C12N 15/82    (2006.01)
A01H 5/00    (2006.01)
C12P 19/04    (2006.01)

(52) U.S. Cl. ...................... 800/284; 800/287; 800/288; 800/317.2; 435/101; 435/194; 435/468

(58) Field of Classification Search ................ 800/284, 800/287, 288, 317.2; 435/101, 194, 468
See application file for complete search history.

(56) References Cited

U.S. PATENT DOCUMENTS

| | | | |
|---|---|---|---|
| 4,696,674 A | 9/1987 | Cipar | |
| 4,801,540 A | 1/1989 | Hiatt et al. | |
| 4,940,835 A | 7/1990 | Shah et al. | |
| 4,971,908 A | 11/1990 | Kishore et al. | |
| 5,349,123 A | 9/1994 | Shewmaker et al. | |
| 5,365,016 A | 11/1994 | Burrell et al. | |
| 5,387,756 A | 2/1995 | Burrell et al. | |
| 5,498,830 A | 3/1996 | Barry et al. | |
| 5,608,149 A | 3/1997 | Barry et al. | |
| 5,608,150 A | 3/1997 | Conner | |
| 5,648,249 A | 7/1997 | Barry et al. | |
| 5,658,773 A | 8/1997 | Bennett et al. | |
| 6,489,539 B1 | 12/2002 | Burrell | |
| 6,538,178 B1 | 3/2003 | Kishore | |
| 6,538,179 B1 | 3/2003 | Barry et al. | |

FOREIGN PATENT DOCUMENTS

| | | |
|---|---|---|
| DE | D. 41 24 531 A1 | 2/1992 |
| EP | 0 120 551 A2 | 10/1984 |
| EP | 0 218 571 A2 | 4/1987 |
| EP | 0 368 506 A2 | 5/1990 |
| EP | 0 438 904 | 12/1990 |
| EP | 0 455 316 A2 | 11/1991 |
| EP | 0 466 995 A2 | 1/1992 |
| EP | 0 634 491 A1 | 1/1995 |
| EP | 0 654 531 A1 | 5/1995 |
| EP | 0 779 363 A2 | 6/1997 |
| JP | 5-153981 | 6/1993 |
| JP | 6-90767 | 4/1994 |
| JP | 7-227286 | 8/1995 |
| WO | WO 91/04036 | 4/1991 |
| WO | WO 91/19806 | 12/1991 |
| WO | WO 92/01782 | 2/1992 |
| WO | WO 92/11375 | 7/1992 |
| WO | WO 92/11376 | 7/1992 |
| WO | WO 92/14827 | 9/1992 |
| WO | WO 94/00563 | 1/1994 |
| WO | WO 94/24292 | 10/1994 |
| WO | WO 94/28146 | 12/1994 |
| WO | WO 94/28149 | 12/1994 |
| WO | WO 95/05457 | 2/1995 |
| WO | WO 95/34660 | 12/1995 |
| WO | WO 96/15248 | 5/1996 |
| WO | WO 96/21738 | 7/1996 |
| WO | WO 97/15678 | 5/1997 |
| WO | WO 97/20936 | 6/1997 |
| WO | WO 97/26362 | 7/1997 |

OTHER PUBLICATIONS

Bai et al. 1990, "The Primary Structure of Rat Liver Glycogen Synthase Deduced by cDNA Cloning: Absence of Phosphorylation Sites 1a and 1b," J. Biol. Chem. 265:7843-7848.

Browner et al. 1989, "Human Muscle Glycogen Synthase cDNA Sequence: A Negatively Charged Protein with an Asymmetric Charge Distribution," PNAS 86: 1443-1447.

Duffus et al. 1984, "Regulation of Carbohydrate Metabolism In: Carbohydrate Metabolism in Plants," Longman: London & New York, pp. 145-154.

(Continued)

Primary Examiner—David T. Fox
(74) Attorney, Agent, or Firm—Kenyon & Kenyon

(57) ABSTRACT

A transgenic plant is prepared by a method in which a plant cell is transformed with a chimaeric gene comprising a promoter and a gene encoding a polypeptide which displays the activity of an enzyme which regulates the amount of a metabolic intermediate in glycolysis or in a pathway for the synthesis or degradation of starch, sucrose or reducing sugar from a glycolytic intermediate.

8 Claims, 3 Drawing Sheets

OTHER PUBLICATIONS

Gay et al. 1983, "Cloning Structural Gen *sac* B, Which Codes for Exoenzyme Levanssucrose of *Bacillus subtilis:* Expression of the Gene in *Escherichia coli,"* J. Bacterial 153(3): 1426-1431.

Gilmour et al. 1992, "cDNA Sequence Analysis and Expression of Two Cold-Regulated Genes of *Arabidopsis thaliana,* " Plant Molec. Biol. 18:13-21.

Hovenkamp-Hermelink et al. 1987, "Isolation of an amylose-free starch mutant of the potato (*Solanum tuberosum L.* )"Theor Appl. Genet. 75:217-221.

Schreier et al. 1985, "The Use Of Nuclear-Encoded Sequences To Direct The Light-Regulated Synthesis And Transport Of A Foreigh Protein Into Plant Chloroplasts," EMBO J. 4(2):25-32.

Sengupta-Gopalan et al. 1985, "Developmentally Regulated Expression of the Bean β Phaseolin gene in tobacco seed," Proc. Natl. Acad. Sci. USA 82:3320-3324.

Sowokinos et al. 1985, "Translucent Tissue defect in *Solanum tuberosum* L." Plant Physiol. 78:489-494.

Visser et al. 1989, "Molecular Cloning and Partial Characterization of the Gene for Granule-Bound Starch Synthase From a Wildtype and an Amylose-Free Potato (*Solanum Tuberosum* L.)," Plant Science 64:185-192.

Vixxer et al. 1991, "Inhibition of the Expression of the Gene for Granule-Bound Starch Synthase in Potato by Antisense Constructs," Mol. Gen. Gent. 225:289-296.

Blakeley et al. Cloning and characterization of a cDNA for the cytosolic isozyme of plant pyruvate kinase: the relationship between the plant and non-plant enzyme. Plant Mol Biol. Oct 15, 1990, (4):665-9.

Burke et al. The isolation, characterization, and sequence of the pyruvate kinase gene of Saccharomyces cerevisiae. J. Biol Chem. Feb 25, 1983, 258940:2193-201.

Carlisle et al. Pyrophosphate-dependent phosphofructokinase. Conservation of protein sequence between the alpha- and beta-subunits and with the ATP-dependent phosphofructokinase, J Biol Chem. Oct 25, 1990, (30):18366-71.

Cognet et al. Structure of the rat L-type pyruvate kinase gene. J Mol Biol. Jul. 5, 1987, 196(1):11-25.

Gottlob-McHugh et al. Normal growth of transgenic tobacco plants in the absence of cytosoloc pyruvate kinase. Plant Physiol. 1992, 100:820-825.

Hajirezaei et al. Transgenic potato plants with strongly decreased expression of pyrophosphate: fructose-6-phosphate phosphotransferase show no visible phenotype and only minor changes in metabolic fluxes in their tubers. Planta 1994. 192:16-30.

Harbron et al. The purification and properties of sucrose-phosphate synthetase from spinach leaves: the involvement of this enzyme and fructose bisphosphatase in the regulation of sucrose biosynthesis. Arch Biochem Biophhys. Nov. 21, 1984, 12(1):237-46.

Inoue et al. Complete amino acid sequence of rat L-type pyruvate kinase deduced from the cDNA sequence. Eur J Biochem. Jan. 15, 1986, 154(2):465-9.

Kruger et al. Molecular properties of pyrophosphate: fructose-6-phosphate phosphotransferase from potato tuber. Arch Biochem Biophys. 1987 Jul;256(1):273-9.

Martin et al. Characterizationof the levanase gene of Bacillus subtilis which shows homology to yeast invertase. Mol Gen Genet. 1987 Jun;208(1-2):177-84.

Micallef et al. Altered photosynthesis, flowering, and fruiting in transgenic tomato plants that have an increased capacity for sucrose synthesis. Planta 1995, 196:327-334.

Ohara et al. Direct genomic sequencing of bacterial DNA: the pyruvate kinase I gene of *Escherichia coli.* Proc Natl Acad Sci U S A. 1989 Sep;86(18):6883-7.

Paul et al. Trransgenic tobacco plants with strongly decreased expression of pyrophosphate: Fructose-6-phosphate 1-phosphotransferase do not differ significantly from wild type inphotosynthate partitioning, plant growth for their ability to cope with limiting phosphate, limiting nitrogen and suboptimaltemperatures. Planta 1995, 196:277-83.

Rohde et al. Structural analysis of the waxy locus from Hordeum vulgare. Nucleic Acids Res. Jul. 25, 1988;16(14b): 7185-6.

Salanoubat et al. Molecular cloning and sequencing of sucrose synthase cDNA from potato (Solanum tuberosum L.): preliminary characterization of sucrose synthase mRNA distribution. Gene. 1987;60(1):47-56.

Taussig and Carlson, Nucleotide sequence of the yeast SUC2 gene for invertase, Nucleic Acids Res. 1983 Mar. 25;11(6):1943-54.

Walker and Huber, Purification and preliminary characterization of sucrose-phosphate synthase using monoclonal antibodies. Plant Physiol. 1989, 89:518-524.

Worrell et al. Expression of a maize sucrose phosphate synthase in tomato alters leaf carbohydrate partitioning. Plant Cell. Oct 3, 1991, (10):1121-30.

Zrenner et al. Evidence of the crucial role of sucrose synthase for sink strength using transgenic potato plants (Solanum tuberosum L.). Plant J. Jan. 7, 1995(1):97-107.

Anderson et al., 1990, Vayda & Park (eds) "Enhancing Carbon Flow into Startch: the Role of ADPglucose Pyrophosphorylase" The Molecular Biology of the Potato, C.A.B. International, Wallingford, pp. 159-180.

Baecker et al., 1983, "Biosynthesis of Bacterial Glycogen" The Journal of Biol. Chem. 258(8):5084-5088.

Ball et al., 1991, "A *Chlamymoans reinhardtii* low-starch mutant is defective for 3-phosphoglycerate activantion and orthophosphate inhibition of ADP-glucose pyrophosphorylase" Planta 185:17-26.

Casper et al., 1985, "Alterations in Growth, Photosynthesis, and Respiration in a Starchless Mutant of *Arabidipsis thaliana* (L.) Deficient in Chloroplast Phosphoglucomutase Activity" Plant Physiol 79:11-17.

Chang et al., 1985, "Gene Expression from Both Intronless and Intron-Containing Rous Sarcoma Viral Clones Is Specifically Inhibited by Anti-Sense RNA" Mol. Cell. Biol. 5(9):2341-2348.

de Fekete, 1968, "The Role of Phosphorylase in Starch Metabolism in Plasmids" Planta 208-221.

Dickinson et al., 1969, "Presence of ADP-Glucose Phosphorylase in Shrunken-2 and Brittle-2 Mutants of Maize Endosperm" Plant Physiol, 44:1058-1062.

Fredeen et al., 1989, "Influence of Phosphorus Nutrition On Growth And Carbon Partitioning In Glycine Max" Plant Physiol 89:225-230.

Ghosh et al., 1966, "Adenosine Diphosphate Glucose Phosphorylase" J. Biol. Chem., 241 (19):4491-4504.

Hawker et al., 1979, "Starch Synthesis in Developing Potato Tubers" Physiol. Plant 46:25-30.

Hnilo et al. 1989, "Mannose Feeding and Its Effect on Starch Synthesis in Developing Potato Tuber Discs" Plant Cell Physiol 30(7):1007-1010.

Iglesias et al. 1993, "Expression of the Potato Tuber ADP-glucose Pyrophosphorylase in *Escherihia coli,*" The Journal of Biological Chemistry, 268(2): 1081-1086.

John, 1992, John Wiley & Sons (eds) Biosynthesis of the Major Group Products pp. 33-54.

Kleinkopf et al., 1987, "Specific Gravity of Russet Burbank Potatoes" American Potato Journal 64:579-587.

Koβmann et al., 1991, "Cloning and Expression Analysis of a Potato cDNA That Encodes Branching Enzyme: Evidence for Co-Expression of Starch Biocynthesis Genes" Mol Gen Genet 230-239.

Kruckebert et al., 1989, "Decreased-Activity Mutants of Phosphoglucose Isomerase in the Cytosol and Chloroplast of *Clarkia xantian* " 261:457-467.

Kumar et al., 1986, "Biosynthesis of Bacterial Glycogen" J. Biol. Chem. 264:10464-10471.

Leung et al., 1986, "Cloning and Expression of the *Escherichia coli glg C* Gene from a Mutant Containing an ADPglucose Pyrophosphorylase with Altered Allosteric Properties" Journal of Bacteriology, 82-88.

Meyer et al., 1993, "A Cloning, Expression, and Sequence of an Allosteric Mutant ADPglucose, Pyrophosphorylase from *Escherichia coli*" Arch. Bioch. Biophys. 302(1):64-71.

Morell et al., 1987, "Biochemistry and Molecular Biology of Starch Synthesis" Plant Gene Systems and Their Biology, 227-242.

Müller-Röber, 1990, "One of two different ADP-glucose pyrophosphorylase genes from potato responds strongly to elevated levels of sucrose" Mol. Gen Genet. 224:136-146.

Müller-Röber et al., 1994, "Approaches to Influence Starch Quantity and Starch Quality in Transgenic Plants" Plant, Cell and Environment 17:601-613.

Nakata et al., 1991, "Comparison of the Primary Sequences of Two Potato Tuber ADP-glucose Pyrophosphorylase Subunits," Plants Molecular Biology, 17:1089-1093.

Olive et al., 1989, "Isolation and nucleotide sequence of cDNA clones encoding ADP-glucose pyrophosphorylase polypeptides from wheat leaf and endosperm" Plant Mol. Biol. 12:525-538.

Pollan, 1998, "Fried, Mashed or Zapped With DNA?" The New York Times Magazine, section 6 44-83.

Preiss and Levi, 1980, "Starch Biosynthesis and Degradation" The Biochem. of Plants, pp. 371-423.

Preiss et al., 1973, "ADPG Synthetase and ADPG-a-Glucan 4 Glucosyl Transferase: Enzymes Involved in Bacterial Glycogen and Plant Starch Synthesis," Anal. New York Acad. Sci., 210:265-278.

Preiss and Romeo, 1989, "Physiology, Biochemistry and Genetics of Bacterial Glycogen Synthesis," Advances in Microbial Physiology, 30:183-238.

Russell et al., 1993, "Plasmid Targeting Of E.*coli* β-glucuronidase and ADP-glucose pyrophosphorylase in maize (*Zea mays* L.) cells" Plant Cell Reports 13:24-27.

Sheehy et al., 1988, "Reduction of polygalacturonase activity in tomato fruit by antisense RNA" Proc. Natl. Acad. Sci. USA 85(23):8805-8809.

Smith et al., 1989, "Evidence that the rb Locus Alters the Starch Content of Developing Pea Embryos through an Effect on ADP Glucose Pyrophosphorylase" Plant Physiol., 89:1279-1284.

Smith-White and Preiss, 1992, "Comparison of Proteins of ADP-Glucose Pyrophosphorylase from Diverse Sources," J. Mol. Evol. 34(5):449-464.

Stark et al., 1992, "Regulation of the Amount of Starch in Plant Tissues by ADP Glucose Pyrophosphorylase" Science 258:287-292.

Stitt et al., Academic Press: San Diego 1987, "Control of Photosynthetic Sucrose Formation" The Biochemistry of Plants, 10:328-409.

Stitt et al., 1995, "Regulation of Metabolism in Transgenic Plants" Ann. Rev. Plant Physiol. Plant Mol. Biol. 46:341-367.

Sweetlove et al., 1996, "Characterization of transgenic potato (*Solanum tuberosum*) tubers with increased ADPglucose pyrophosphorylase" Biochem. J. 320:487-492.

Vayda and Park, 1990 "The Molecular and Cellular Biology of the Potato" CAB International Table of Contents, First Edition (5 pages) and Belknap et al., eds., 1994, C.A.D. International: Wallingford, U.K. "The Molecular and Cellular Biology of the Potato" Table of Contents, Second Edition (5 pages).

von Schaewen et al., 1990, "Expression of yeast-derived invertase in the cell wall of tobacco and Arabidopsis" EMBO J 9(10):3033-3044.

Wasmann et al., 1986, "The importance of the transis peptide and the transported protein for protein import into chloroplasts," Mol. Gen. Genet. 205:446-453.

Witt, 1989, "Changes in Activity of Enzymes Involved in Carbohydrate Metabolism During Dedifferentiation of Mature Cells of *Riella helicophylla* (Bory et Mont) Mont." J. Plant Physiol 135:597-600.

English Language Abstract of DE 41 24 537.
English Language Abstract of JP 5-153981.
English Language Abstract of JP 6-90767.
English Language Abstract of JP 7-227286.

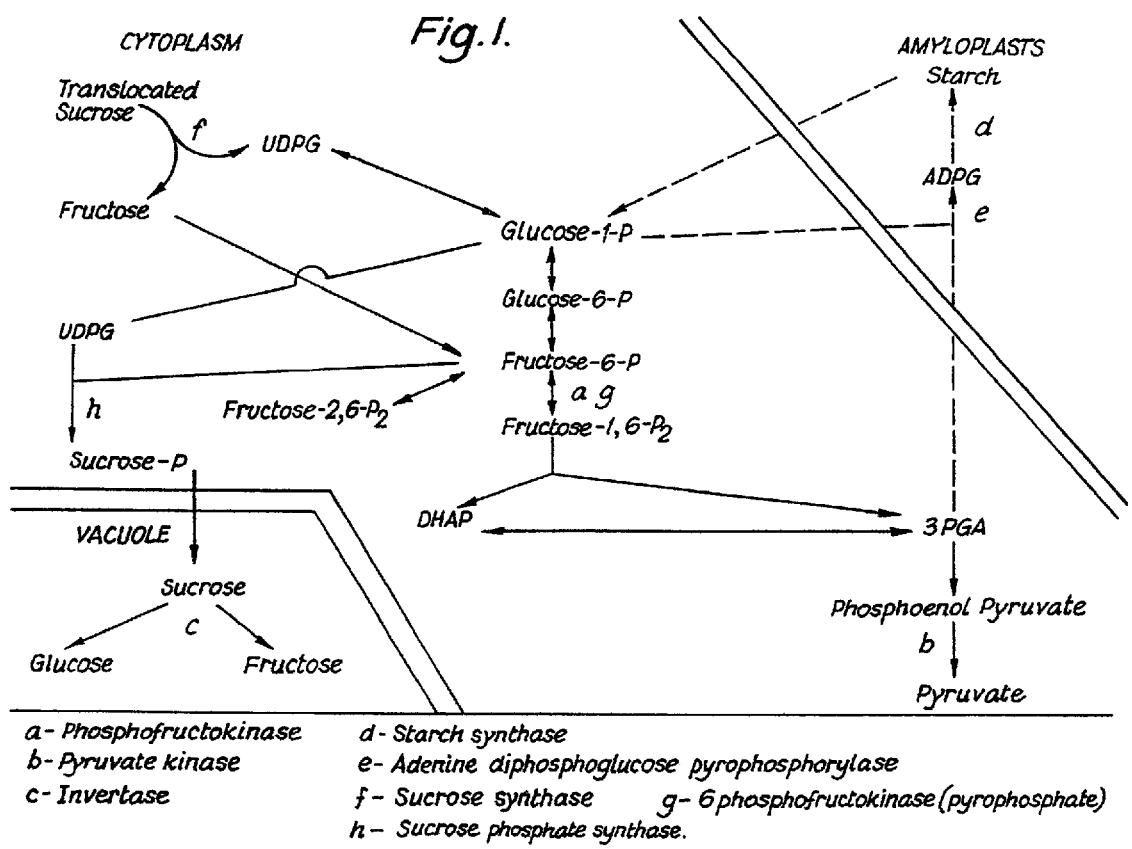

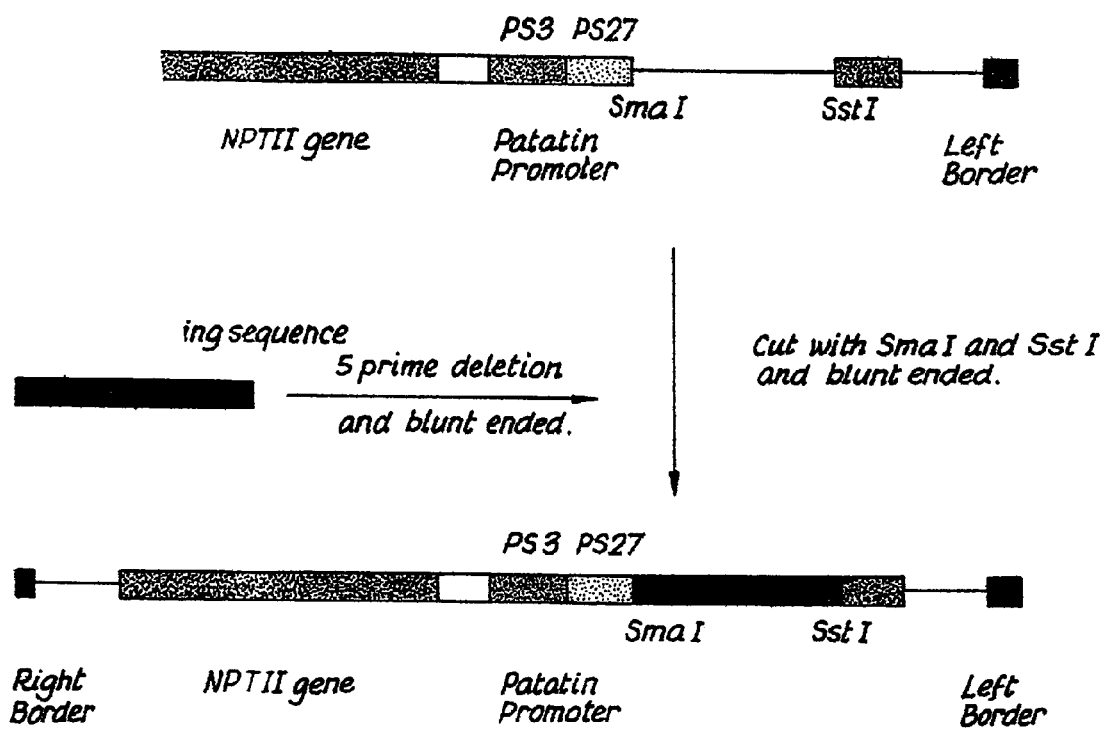

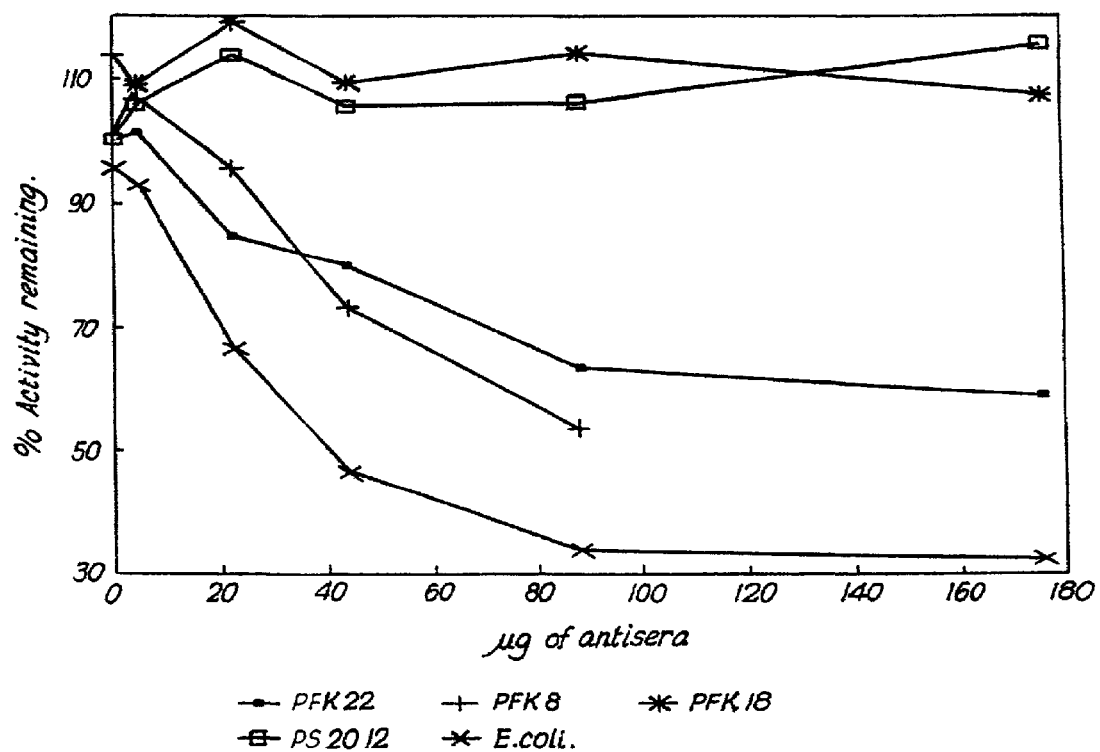

MODIFICATION OF PLANT METABOLISM

CROSS-REFERENCE TO RELATED APPLICATION

This application is a continuation of U.S. patent application Ser. No. 08/284,199 filed on Aug. 2, 1994, abandoned, which is a continuation of U.S. patent application Ser. No. 07/991,451 filed on Dec. 16, 1992, now U.S. Pat. No. 5,387,756, which is a continuation of U.S. patent application Ser. No. 07/628,216 filed on Dec. 17, 1990, abandoned, which further claims foreign priority to GB 89 28 937.5 filed Dec. 21, 1989 and to GB 901 49 88.1 filed Jul. 6, 1990, all of which are incorporated herein by reference in their entirety.

BACKGROUND OF THE INVENTION

1. Field of the Invention

The present invention relates to transgenic plants and their preparation.

2. Brief Description of the Related Art

Phosphofrucktokinase (PFK :EC 2.7.1.11) is widely regarded as a key regulatory enzyme controlling the entry of carbon into glycolysis. Glycolysis, especially in plant cells, serves to supply both respiratory carbon for energy production and intermediates for other metabolic pathways. The potato tuber contains four forms of PFK (Kruger et al, Arch. Biochem. Biophys. 267, 690–700) and pyrophosphate fructose-6-phosphate phosphotransferase (PFP:EC 2.7.1.90) which can catalyse the conversion of fructose-6-phosphate to fructose-1,6-bisphosphate. PFK is present in both the cytosol and the amyloplast while PFP is only known to occur in the cytosol.

It has previously been thought that PFK alone controls the total glycolytic flux. However, we have now found that this is not the case. We introduced additional PFK into potato plants by genetic manipulation. Our results indicate that a substantial increase in PFK activity did not substantially alter flux through glycolysis but changed the pool sizes of intermediates. The results indicate that regulation of glycolytic flux may be achieved not only at the entry of carbon into the pathway but also exit from it. This finding has general applicability.

SUMMARY OF THE INVENTION

Accordingly, the present invention provides a process for the preparation of a transgenic plant, which method comprises:
 (i) transforming a plant cell with a chimaeric gene comprising (a) a suitable promoter and (b) a coding sequence the product of which causes modification of the amount of metabolic intermediate in glycolysis or in a pathway for the synthesis or degradation of starch, sucrose or reducing sugar; and
 (ii) regenerating a plant from the transformed cell.

The invention also provides the chimaeric gene. A vector suitable for use in the present process comprises the chimaeric gene such that the chimaeric gene is capable of being expressed in a plant cell transformed with a vector. A plant cell according to the invention therefore harbours the chimaeric gene such that the chimaeric gene is capable of being expressed therein.

A transgenic plant can therefore be obtained which harbours in its cells the chimaeric gene such that the chimaeric gene is capable of being expressed in the cells of the plant. Seed or other propagules can be obtained from the transgenic plant and used to grow further plants stably transformed with the chimaeric gene.

BRIEF DESCRIPTION OF THE DRAWINGS

FIG. 1 shows a simplified diagram of carbohydrate metabolism with reference to plant storage tissues such, for example, as potato tubers. In FIG. 1 the broken lines indicate tentatively assumed pathways.

FIG. 2 shows the procedure used to produce a chimaeric PFK gene.

FIG. 3 shows the immunodetection of E. coli PFK activity. PFK was immunoactivated with antisera raised to the introduced E. coli PFK. Antisera was mixed with equal amounts of PFK activity (1 nmole F6 P consumed $min^{-1}$) from two transgenic lines expressing PFK (PFK22, 0; pfk8, +), two transgenic lines one not expressing PFK (PFK16*) and expressing GUS (PS20-12), or E. coli PFK (x). Bound PFK was removed with protein A and the activity not removed assayed (Kruger et al.), Archives of Biochemistry and Biophysics 267 690–700, 1989.

DETAILED DESCRIPTION OF THE PREFERRED EMBODIMENTS OF THE INVENTION

The invention enables plant metabolism to be altered in a glycolytic pathway or in a pathway for the synthesis or degradation of starch, sucrose or a reducing sugar such as glucose or fructose. It enables the accumulation of pathway metabolites to be altered. Several applicable pathways are shown in FIG. 1 of the accompanying drawings. The invention is particularly applicable to potatoes. It had been expected that the introduction and expression of additional PFK into potato tuber cells would cause a high flux in the glycolytic pathway. Furthermore, if this gene had been introduced and expressed in the whole plant, it would not have been unreasonable to have expected that the plant would have died. In the event, though, it was surprising to find that after the introduction and expression of the PFK gene the plant did not die and the flux in the glycolysis metabolism pathway was not increased.

The storage of potato tubers in low temperature storage conditions normally results in less PFK activity. This, it is believed, leads to an increased production in the potato tubers of sucrose and reducing sugars. The accumulation of these sugars in the potato tubers presents a significant problem to processors of potatoes. For example, producers of crisps and chips (otherwise known respectively as potato chips and French fries) have found that the presence of an increased level of sugars tends to cause an undue browning of the products during the frying process.

When potato tubers of the subject invention are stored at low temperatures, the increased amount of PFK present therein ensures a continued flux into the glycolysis metabolism pathway. This in turn means that the flux level in the sucrose synthesis pathway is lower than has heretofore been the case with stored potato tubers. Thus significantly reduced levels of sucrose and reducing sugars accumulates in the stored tubers.

In the invention, a chimaeric gene is constructed which comprises (a) a suitable promoter operably linked to (b) a coding sequence the product of which causes modification of the amount of a metabolic intermediate in glycolysis or in a pathway for the synthesis or degradation of starch, sucrose or reducing sugar. The chimaeric gene may be constructed in any convenient fashion. The coding sequence is provided such that it is expressible in plant cells. In a particular embodiment, the chimaeric gene encodes for two or more enzymes.

The promoter (a) should be capable of expressing the coding sequence of interest in a plant. The promoter may be a promoter capable of directing expression in a particular tissue of a plant and/or at particular stages of development. The promoter may be heterologous or homologous to the plant. A suitable promoter may be the 35S cauliflower mosaic virus promoter, a nopaline synthase or octopine synthase promoter, a patatin promoter or a small sub-unit of rubisco. A promoter from tubers, e.g. patatin, is preferred for directing expression in potatoes, in particular potato tubers. A suitable promoter may be, for example, a constitutive promoter or a tissue-specific promoter.

The coding sequence (b) can encode an enzyme which regulates the amount of a metabolic intermediate of a specific pathway. The pathway may be the glycolytic pathway. Glycolysis is the sequence of reactions which converts glucose to pyruvate with concomitant production of ATP or NADH and is also termed the Embden-Meyerhof-Parnas pathway.

Sucrose consists of glucose and fructose coupled via an alpha 1-2 O-glycosidic bond. Pathways of sucrose synthesis therefore involve enzyme steps that produce suitable intermediates to form this linkage. Starch is a polymer which consists mainly of alpha 1-4 linked glucose with varying amounts of 1-6 linked glucose. Thus pathways of starch synthesis involve steps that produce suitable intermediates to form this polymer.

A coding sequence is selected which when expressed in plant cells will increase or decrease the metabolism of a pathway mentioned above. The coding sequence (b) may encode for a pathway enzyme or an active modified form of a pathway enzyme, for example a truncated pathway enzyme. The pathway enzyme may be, for example, PFK (EC 2.7.1.11), pyruvate kinase (PK) (EC 2.7.1.21), acid invertase (EC 3.2.1.26), starch synthase (EC 2.4.1.21), adenosine, diphosphoglucose pyrophosphorylase (EC 2.7.7.27), sucrose synthase (EC 2.4.1.13), 6-phosphofructokinase (pyrophosphate) (EC 2.7.1.90) or sucrose phosphate synthetase (SPS) (EC 2.4.1.14).

The coding sequence may be from a plant gene or a non-plant gene such as a microbial gene. It may be from a bacterial gene, for example a gene from *E. coli*, or a yeast gene, for example *Saccharomyces cerevisiae*. In particular, a PFK coding sequence may be provided by the pfkA gene from *E. coli* or by a pfk gene from *Solanum tuberosum*. An acid invertase coding sequence may be provided from *Saccharomyces cerevisiae*.

Plant cells can be transformed with the chimaeric gene by direct DNA uptake, typically by way of a DNA fragment comprising the chimaeric gene. Alternatively, there may be used a vector incorporating the chimaeric gene. The chimaeric gene typically includes transcriptional control sequences, for example a promoter as above, and translational initiation and/or termination sequences. Plant terminator and polyadenylation sequences may be present. A vector typically contains a region which enables the chimaeric gene to be transferred to and stably integrated in the plant cell genome.

The vector is therefore typically provided with transcriptional regulatory sequences and/or, if not present at the 3'-end of the coding sequence of the gene, a stop codon. A DNA fragment may therefore also incorporate a terminator sequence and other sequences which are capable of enabling the gene to be expressed in plant cells. An enhancer or other element able to increase or decrease levels of expression obtained in particular parts of a plant or under certain conditions, may be provided in the DNA fragment and/or vector. The vector is also typically provided with an antibiotic resistance gene which confers resistance on transformed plant cells, allowing transformed cells, tissues and plants to be selected by growth on appropriate media containing the antibiotic.

Transformed plant cells can be selected by growth in an appropriate medium. Plant tissue can therefore be obtained comprising a plant cell which harbours a gene encoding an enzyme under the control of a promoter, for example in the plant cell genome. The gene is therefore expressible in the plant cell. Plants can then be regenerated which include the gene and the promoter in their cells, for example integrated in the plant cell genome such that the gene can be expressed. The regenerated plants can be reproduced and, for example, seed obtained.

A preferred way of transforming a plant cell is to use *Agrobacterium tumefaciens* containing a vector comprising a chimaeric gene as above. A hybrid plasmid vector may therefore be employed which comprises:
(a) a chimaeric gene containing regulatory elements capable of enabling the gene to be expressed when integrated in the genome of a plant cell;
(b) at least one DNA sequence which delineates the DNA to be integrated into the plant genome; and
(c) a DNA sequence which enables this DNA to be transferred to the plant genome.

Typically the DNA to be integrated into the plant cell genome is delineated by the T-DNA border sequences of a Ti-plasmid. If only one border sequence is present, it is preferably the right border sequence. The DNA sequence which enables the DNA to be transferred to the plant cell genome is generally the virulence (vir) region of a Ti-plasmid.

The gene coding for the enzyme and its transcriptional and translational control elements can therefore be provided between the T-DNA borders of a Ti-plasmid. The plasmid may be a disarmed Ti-plasmid from which the genes for tumorigenicity have been deleted. The gene and its transcriptional control elements can, however, be provided between T-DNA borders in a binary vector in trans with a Ti-plasmid with a vir region. Such a binary vector therefore comprises:
(a) the chimaeric gene under the control of regulatory elements capable of enabling the gene to be expressed when integrated in the genome of a plant cell; and
(b) at least one DNA sequence which delineates the DNA to be integrated into the plant genome.

*Agrobacterium tumefaciens*, therefore, containing a hybrid plasmid vector or a binary vector in trans with a Ti-plasmid possessing a vir region can be used to transform plant cells. Tissue explants such as stems or leaf discs may be inoculated with the bacterium. Alternatively, the bacterium may be co-cultured with regenerating plant protoplasts. Plant protoplasts may also be transformed by direct introduction of DNA fragments which encode the enzyme and in which the appropriate transcriptional and translational control elements are present or by a vector incorporating such a fragment. Direct introduction may be achieved using electroporation, polyethylene glycol, microinjection or particle bombardment.

Plant cells from angiospermous, gymnospermous, monocotyledonous or dicotyledonous plants can be transformed according to the present invention. Monocotyledonous species include barley, wheat, maize and rice. Dicotyledonous species include cotton, lettuce, melon, pea, petunia, potato, rape, soyabean, sugar beet, sunflower, tobacco and tomato. Potato cultivars to which the invention is applicable include Desiree, Maris Bard, Record and Russet Burbank.

Tissue cultures of transformed plant cells are propagated to regenerate differentiated transformed whole plants. The transformed plant cells may be cultured on a suitable medium, preferably a selectable growth medium. Plants may be regenerated from the resulting callus. Transgenic plants are thereby obtained whose cells incorporate the chimaeric gene in their genome, the chimaeric gene being expressible in the cells of the plants. Seed or other propagules from the regenerated plants can be collected for future use.

A preferred procedure in respect of the potato variety Record is as follows.

Plant Material

Record shoot cultures are maintained in vitro on Murashige and Skoog (MS) medium in Magenta GA-7 containers at 22° C. (16 h/8 h light/dark). These are nodally sub-cultured every 3 weeks.

In vitro shoots of 2–3 inches (5–7.5 cm) height are potted in 2.5 inches (6.4 cm) pots of Levingtons F1 compost. They are weaned in a propagator for one week in a growth room at 18° C. (16 h/8 h light/dark). The propagator is removed and the plants repotted at 3 weeks into 5 inch (12.7 cm) pots. At 5–7 weeks the plants are used for transformation.

*Agrobacterium tumefaciens*

Liquid overnight cultures of suitable strains e.g. LBA4404, C58#3 are grown at 28° C. to an $OD_{600}$ of 0.8 in L-broth (see appendix).

Cocultivation

The youngest four most expanded leaves are taken and surface sterilised in 10% Domestos (commercial bleach) for 15 minutes. Leaves are rinsed thoroughly with sterile water and then cut into discs with a 7 mm cork borer. The discs are mixed with the *Agrobacterium* for 1–5 minutes, blotted dry on filter paper (Whatman No.1) and then placed on callusing medium (see appendix) in 90 mm triple vented petri dishes, lower epidermis down. The 90 mm triple vented petri dishes are sealed with tape, cut to allow gas exchange and then incubated at 22° C. (16 h/8 h light/dark). The discs are transferred to callusing medium plus 500 $\mu g$ $ml^{-1}$ of claforan and 30 $\mu g$ $ml^{-1}$ kanamycin after 48 hours. This removes bacteria and selects for transformed cells.

Regeneration of Transformed Shoots

After 1 week, the discs are transferred to shooting medium (see appendix) containing the same antibiotics. Further transfers are made onto the same medium until shoots can be excised (usually about 4 weeks). Shoots with calli are transferred to MS medium with cefotaxime in well ventilated containers, e.g. Magenta. Transformants are maintained, after several passages with cefotaxime to remove bacteria, on MS medium. They may be removed from in vitro, weaned and grown to maturity as described for the stock plants. The process yields transformed Record plants at a frequency of up to 30% of the discs cocultivated.

APPENDIX

| L-broth: | 10 g $l^{-1}$ bacotryptone |
| | 5 g $l^{-1}$ yeast extract |
| | 5 g $l^{-1}$ sodium chloride |
| | 1 g $l^{-1}$ glucose |

APPENDIX-continued

| Callusing medium: | MS with 3% sucrose |
| | 0.5 mg $l^{-1}$ 2,4-D |
| | 2.5 mg $l^{-1}$ BAP |
| Shooting medium: | MS plus 3% sucrose |
| | 2.5 mg $l^{-1}$ BAP |
| | 1.0 mg $l^{-1}$ $GA_3$ |

The following examples illustrate[s] the invention.

EXAMPLE 1

Production of PFK in Potato Tubers

The procedure used to produce a chimaeric PFK gene to provide tuber-specific expression of PFK is illustrated in FIG. 2. The PFK coding sequence was obtained from a clone of the pfkA gene as described by Hellinga H. W. and Evans P. R. (Eur. J. Biochem 149 363–373, 1985). The PFK coding sequence was isolated so that only 20 base pairs remained before the translational start site. More specifically the *E. coli* pfkA gene on plasmid pHE1012 was deleted at the 5' end to 20 bp from the translational start site and 50 bp from the 3' end of the coding sequence. This was then blunt end ligated into the plasmid pFW4101 in place of the GUS (B-glucuronidase) coding sequence to give plasmid pFW4023. pFW4101 was constructed with a patatin promoter made from two genomic clones PS3 and PS27. The patatin fragments PS3 and PS27 were derived from the genomic clones described by Mignery et al (Gene 62, 27–44, 1988). The fragments consist of –3.5 kb to –1 kb of PS3 and –1 kb to +3 kb of PS27 numbered in relation to the translation start.

*E. coli* harbouring pFW4023 and *E. coli* harbouring pFW4101 were deposited at the National Collection of Industrial and Marine Bacteria, Aberdeen, GB on 5 Jul. 1990 under accession numbers NCIMB 40305 and NCIMB 40306.

The vectors pFW4101 and pFW4023 were transferred separately into *Agrobacterium tumefaciens* strain LBA 4404 by triparental mating. The *Agrobacterium* strains were used to transform the potato cultivar Desiree. A large family of over 60 transgenic plants were produced. Southern analysis showed that the plants contained between one and eight copies of the *E. coli* pfkA gene. Some of these plants produced tubers which contained considerable PFK activity. PFK activity was measured as described by Kruger et al, Archives of Biochemistry and Biophysics 267 690–700, 1989. Intermediates were extracted with ice cold perchlorate and measured enzymatically. The results are shown in Table 1.

TABLE 1

PFK Activity and amount of glycolytic intermedia

| | PFR transgenic | | GUS transgenic | | | |
|---|---|---|---|---|---|---|
| | mean | (SD) | mean | (SD) | t value | P |
| PFK activity[1] | 625 | (206) | 29 | (12) | 4.07 | >99 |
| Glc-6P[2] | 78 | (8.9) | 100 | (21) | 1.97 | >95 |
| Fru-6P[2] | 21 | (4.2) | 29 | (9) | 1.77 | >90 |

TABLE 1-continued

PFK Activity and amount of glycolytic intermedia

|  | PFR transgenic | | GUS transgenic | | | |
|---|---|---|---|---|---|---|
|  | mean | (SD) | mean | (SD) | t value | P |
| Ratio | 3.7 | (0.56) | 3.7 | (0.66) | 0.9 | N.S. |
| PEP[2] | 82 | (20.4) | 28 | (8.0) | 3.54 | >99 |
| Pyr[2] | 44 | (22.6) | 37 | (16) | 0.80 | N.S. |
| Ratio | 2.5 | (1.3) | 1.0 | (0.6) | 2.20 | >95 |

[1]PFK activity is given as nmoles min$^{-1}$ g fr. wt. $^{-1}$.
[2]Intermediates are given as nmoles g fr. wt. $^{-1}$.

Assays containing mixtures of extracts from two plants differing in amount of activity did not reveal the presence of activators or inhibitors (data not shown). Two lines of evidence were sought to demonstrate that the observed increase in PFK activity was due to *E. coli* PFK. Firstly antisera raised to this enzyme was used to immunoinactivate specifically the *E. coli* PFK activity in crude protein extracts from tubers. The results are shown in FIG. 3. A considerable proportion of the activity could be removed in lines showing increased activity but not in lines expressing GUS or not showing elevated activity (FIG. 3). Mixtures of line 12 (GUS) control plants with either *E. coli* PFK or line 22 (elevated PFK) gave the expected results indicating that the immunoinactivation was not due to inhibitors in the control plants. Secondly the antisera was used with Western blots to show clearly the appearance of the 36 kD *E. coli* PFK polypeptide of the correct molecular weight (data not shown). This band does not coincide with any predominant potato protein (data not shown) or potato PFK which has subunit molecular weights between 55 and 63 kD.

To discover whether this increase in enzyme activity, which in the strongest expressing tissue was 40 fold, had altered glycolytic flux we initially measured the rate of respiration by Warburg manometry. Respiratory rates were determined by Warburg manometry (Umbreit). Tubers were bathed in 2.7 ml of 20 mM phosphate buffer pH5.2 containing 0.5 mM glucose. $CO_2$ was absorbed in 10% KOH. These results are shown in Table 2.

TABLE 2

Respiration in Tubers
Gas exchange nmol min$^{-1}$g$^{-1}$ fr.wt.(S.D.)

|  | PFK Transgenic | | GUS Transgenic | |
|---|---|---|---|---|
| Oxygen Uptake | | | | |
| at 2 h | 29.4 | (8.9) | 36.3 | (7.2) |
| at 5 h | 49.8 | (4.1) | 55.2 | (10.4) |
| $CO_2$ Release | | | | |
| at 2 h | 22.2 | (3.2) | 24.3 | (8.6) |
| at 5 h | 33.7 | (7.7) | 44.0 | (9.0) |

There was no indication of a change in oxygen uptake or carbon dioxide evolution. Thus if respiration determined by gas exchange is an indication of glycolytic flux, excess PFK has not altered it. However in these tubers it is possible that a substantial amount of the respired carbohydrate entered the citric acid cycle via the pentose phosphate pathway and not glycolysis. Both pathways consume glucose-6-P. If this were the case then the addition of a large excess of PFK might change the distribution of metabolism but not the overall flux.

We therefore determined the rate of release of $^{14}CO_2$ from 6$^{14}$C-glucose and from 1-$^{14}$C-glucose. The ratio of release 6C/1C indicates the contribution of glycolysis to respiration. In both PFK and GUS transgenic plants the ratio was approximately 0.2 after 40 mins of incubation in $^{14}$C-glucose, 0.3 after 2 h and 0.4 after 4 h. Thus the presence of up to 40 fold excess of PFK activity has not altered the relative contributions of glycolysis and pentose phosphate pathway to glycolytic flux.

These results suggest that PFK is not regulating the entry of carbon into glycolysis in potato tubers. We therefore measured the amounts of glucose-6-P, and fructose-6-P, phosphoenol pyruvate (PEP) and pyruvate (Table 1). Elevated PFK activity has clearly lowered the amount of hexose-phosphate present but the mass action ratio (Glc-6P: Fru-6P) has remained the same and is approximately 4. This is near the equilibrium constant of glucose-6-phosphate isomerase (Sicher and Kremer, Pl. Science 67, 47–56, 1990). More notable however is the large increase in PEP and change in the ratio of PEP:pyruvate. This strongly suggests that the increased level of PFK has led to more carbon entering glycolysis for a given respiratory flux and in those plants where PFK activity is increased the enzymes (probably pyruvate kinase and PEP carboxylase) that use PEP are strongly influencing the flux.

Plants of cv Desiree transformed as described above were grown in the field and the amount of sucrose in the potato tubers measured at harvest was less in lines expressing high PFK. The difference between sucrose content is significant at P=0.05. Thus this modification of glycolysis can cause an alteration in a pool of metabolite in a related pathway of carbohydrate metabolism (as illustrated in FIG. 1).

TABLE 3

Alteration in sucrose content of tubers

| Line | PFK Activity nmol min$^{-1}$ g$^{-1}$ fr.wt | Sucrose content % w/w |
|---|---|---|
| PFK22 | 1011 | 0.219 |
| PFK 36 | 379 | 0.293 |
| PS2O-24 | 18 | 0.347 |
| PS2O-6 | 18 | 0.358 |

Such alterations are not confined to potato tubers. The patatin promoter can be induced to express in leaf tissue by incubating them in a medium of sucrose (Rocha-Sosa et al (1989) EMBO J. 8 23–29). Discs were cut from leaves of plants (line PFK 22) containing the chimaeric PFK gene and control plants containing the chimaeric GUS gene (line PS20-12). After incubation in the light on a medium containing it subrose, to cause the expression of the PFK gene, the tissues were analysed for changes in intermediates.

The results in Table 4 show that in a tissue other than a tuber the alterations in the activity of PFK can alter metabolic intermediates.

TABLE 4

| Ratio of | $\dfrac{\text{Amount of intermediate in line PFK} - 22}{\text{Amount of intermediate in line PS20} - 12}$ | |
|---|---|---|
| Fru- 2,6-P$_2$ | PEP | Pyruvate |
| 2.23 ± 0.37 | 1.18(±0.3) | 0.49(±0.1) |

EXAMPLE 2

Expression of *E. coli* PFK in Rice Callus

A chimaeric gene was constructed as described in FIG. 2 but a 35S promoter replaced the patatin promoter.

This gene was used to transform rice protoplasts and the callus assayed for PFK activity. Control callus tissue had activities of up to 1500 nmol min$^{-1}$ g$^{-1}$ fr. wt. The transformed callus had activities of 3000 nmol min$^{-1}$ g$^{-1}$ fr. wt. Thus it is possible to express this chimaeric gene in monocotyledonous plants such as rice.

What is claimed is:

1. A process for the preparation of transgenic plant, which process comprises:
   (i) transforming a plant cell with a chimeric gene comprising (a) a promoter that directs gene expression in a plant, said promoter being operably linked to (b) a coding sequence which encodes for phosphofructokinase; and
   (ii) regenerating a plant from the transformed plant cell; wherein expression of said chimeric gene in said regenerated plant causes a modification of the amount of a metabolic intermediate:
      (a) in the pre-existing intracellular pathway of glycolysis,
      (b) in the pre-existing intracellular pathway for the synthesis or degradation of starch, or
      (c) in the pre-existing intracellular pathway for the synthesis or degradation of sucrose or reducing sugar.

2. The process of claim 1, wherein said chimeric gene also comprises a coding sequence encoding a second enzyme.

3. The process of claim 1, wherein said chimeric gene is expressed in a tuber of said regenerated plant.

4. The process of claim 1, wherein said chimeric gene is expressed in a seed of said regenerated plant.

5. The process of claim 1, wherein the coding sequence is from a plant gene.

6. The method of claim 1, wherein the coding sequence is from a non-plant gene.

7. A transgenic plant comprising a chimeric gene which comprises;
   (a) a promoter that directs gene expression in a plant, said promoter being operably linked to
   (b) a coding sequence which encodes phosphofructokinase, wherein expression of said chimeric gene in said transgenic plant causes a modification of the amount of a metabolic intermediate:
      (i) in the pre-existing intracellular pathway of glycolysis,
      (ii) in the pre-existing intracellular pathway for the synthesis or degradation of starch, or
      (iii) in the pre-existing intracellular pathway for the synthesis or degradation of sucrose or reducing sugar.

8. The transgenic plant of claim 7, wherein the chimeric gene also comprises a coding sequence that encodes a second enzyme.

* * * * *